United States Patent
Shoeb et al.

(10) Patent No.: US 11,935,652 B1
(45) Date of Patent: Mar. 19, 2024

(54) HEALTH STATUS CHANGE DETECTION USING ANOMALY DETECTION IN LATENT SPACES

(71) Applicant: Verily Life Sciences LLC, South San Francisco, CA (US)

(72) Inventors: Ali Shoeb, San Rafael, CA (US); Lance Myers, Pacifica, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 817 days.

(21) Appl. No.: 16/787,561

(22) Filed: Feb. 11, 2020

Related U.S. Application Data

(60) Provisional application No. 62/808,032, filed on Feb. 20, 2019.

(51) Int. Cl.
| | |
|---|---|
| *G16H 50/20* | (2018.01) |
| *G06N 3/088* | (2023.01) |
| *G16H 50/30* | (2018.01) |
| *G16H 50/70* | (2018.01) |
| *G16H 50/80* | (2018.01) |

(52) U.S. Cl.
CPC .......... *G16H 50/20* (2018.01); *G06N 3/088* (2013.01); *G16H 50/30* (2018.01); *G16H 50/70* (2018.01); *G16H 50/80* (2018.01)

(58) Field of Classification Search
None
See application file for complete search history.

(56) References Cited

U.S. PATENT DOCUMENTS

| | | | |
|---|---|---|---|
| 7,953,676 B2 | 5/2011 | Agarwal et al. | |
| 8,454,506 B2 | 6/2013 | Rothman et al. | |
| 8,521,490 B2 | 8/2013 | Hardigan | |
| 10,463,299 B1 * | 11/2019 | Kohli | A61B 5/0205 |
| 2007/0294110 A1 | 12/2007 | Settimi | |
| 2013/0124221 A1 | 5/2013 | Lynn et al. | |

(Continued)

FOREIGN PATENT DOCUMENTS

| | | |
|---|---|---|
| WO | 2011159592 A1 | 12/2011 |
| WO | 2018086761 A1 | 5/2018 |

OTHER PUBLICATIONS

Zong, Bo, et al. "Deep autoencoding gaussian mixture model for unsupervised anomaly detection." International conference on learning representations. 2018. (Year: 2018).*

(Continued)

*Primary Examiner* — Devin C Hein
(74) *Attorney, Agent, or Firm* — Kilpatrick Townsend & Stockton LLP

(57) ABSTRACT

Individual-specific changes in health conditions are detected using a latent space mapping generated from baseline physiological data collected in a longitudinal study of the individual. Historical baseline data in an n-dimensional input space is modeled into a k-dimensional latent space, where k<n. The mapping for the model is then used to convert new physiological data into a latent space point, which can be used to determine if the associated newly collected physiological data is anomalous and thus indicative of a change in health condition. Anomalies can be inferred from poor fit between the point and baseline data within the latent space, or form large error between data reconstructed into the input space from the point and the original new physiological data.

20 Claims, 8 Drawing Sheets

(56) References Cited

U.S. PATENT DOCUMENTS

| | | | |
|---|---|---|---|
| 2014/0046683 A1 | 2/2014 | Michelson et al. | |
| 2014/0279746 A1 | 9/2014 | De Bruin et al. | |
| 2016/0242690 A1* | 8/2016 | Principe | A61B 5/316 |
| 2018/0341836 A1* | 11/2018 | Lim | G06T 7/0002 |
| 2018/0365089 A1* | 12/2018 | Okanohara | G06F 11/07 |
| 2019/0258962 A1 | 8/2019 | Sreekumari et al. | |
| 2020/0020098 A1* | 1/2020 | Odry | G06V 10/7715 |
| 2020/0090812 A1 | 3/2020 | Condie et al. | |
| 2020/0111575 A1 | 4/2020 | Hart et al. | |
| 2020/0185102 A1* | 6/2020 | Leventhal | A61B 5/7267 |
| 2020/0271674 A1 | 8/2020 | Royall et al. | |
| 2020/0279628 A1* | 9/2020 | Bulut | G16H 20/10 |
| 2021/0151194 A1 | 5/2021 | Foschini et al. | |
| 2021/0353224 A1 | 11/2021 | Etkin et al. | |

OTHER PUBLICATIONS

J. Sun, X. Wang, N. Xiong and J. Shao, "Learning Sparse Representation With Variational Auto-Encoder for Anomaly Detection," in IEEE Access, vol. 6, pp. 33353-33361, 2018, doi: 10.1109/ACCESS.2018.2848210. (Year: 2018).*

Hou et al., "Deep feature consistent variational autoencoder", 2017 IEEE Winter Conference on Applications of Computer Vision (WACV). IEEE, 2017.

Kiran et al., "An overview of deep learning based methods for unsupervised and semi-supervised anomaly detection in videos", Journal of Imaging 4.2 (2018): 36.

Schlegl et al., "Unsupervised anomaly detection with generative adversarial networks to guide marker discovery", International conference on information processing in medical imaging. Springer, Cham, 2017.

U.S. Appl. No. 14/687,128, filed Apr. 15, 2015, Rajan et al.

U.S. Appl. No. 14/798,504, filed Jul. 14, 2015, Tekumalla et al.

U.S. Appl. No. 15/442,665, filed Feb. 25, 2017, Brunner.

U.S. Appl. No. 16/787,549, "Final Office Action", dated Nov. 10, 2022, 15 pages.

U.S. Appl. No. 16/787,549 , "Non-Final Office Action", dated Apr. 28, 2022, 15 pages.

Shoeb, "Application of Machine Teaming to Epileptic Seizure Onset Detection and Treatment", Thesis (Ph. D.) Harvard-MIT Division of Health Sciences and Technology, 2009, pp. 1-162.

U.S. Appl. No. 16/787,549, Final Office Action, dated Sep. 29, 2023.

U.S. Appl. No. 16/787,549, Non-Final Office Action, dated Mar. 23, 2023.

* cited by examiner

HEALTH STATUS CHANGE DETECTION USING ANOMALY DETECTION IN LATENT SPACES

CROSS-REFERENCE To RELATED APPLICATIONS

This application claims priority to U.S. Patent Application No. 62/808,032, filed Feb. 20, 2019, titled "Health Status Change Detection Using Anomaly Detection In Latent Spaces," the entirety of which is hereby incorporated by reference.

TECHNICAL FIELD

The present disclosure relates to healthcare generally and more specifically to detecting changes in health status from acquired metrics.

BACKGROUND

Healthcare is an important part of life for many individuals, whether it be preventative or remediary in nature. The ability to accurately detect or identify changing health conditions is important for many aspects of healthcare, including both research and treatment.

In some basic healthcare situations, individuals may go to a medical professional for routine checkups, for diagnosis or treatment of a possible health condition, or for treatment of an urgent health condition. These different instances may be spread out over time, with days, weeks, months, years, or even longer between such instances, and with non-uniform amounts of time between different subsequent instances. While important physiological data may be collected at each of these professional visits, leveraging this data can be difficult, at least in part due to its sparse nature.

The availability of user-facing monitoring devices is becoming ever more prevalent. Individuals regularly wear or otherwise interact with sensors such as heart rate sensors, weight sensors, cameras, blood pressure monitors, home-based electrocardiograms, and other such sensors numerous times throughout their daily lives. As a result, the availability and amount of physiological data available for individuals is becoming vast.

Leveraging all of this physiological data for the benefit of individuals presents numerous challenges. Tremendous amounts of study and research goes in to identifying patterns and correlations between various physiological variables and target diagnoses, with the hope of using these patterns and correlations to help diagnose individuals simply by collecting certain physiological variables. However, such research and study requires vast resources and time, and may not result in useful conclusions.

With the advent of machine learning, attempts have been made to apply machine learning algorithms to large corpuses of physiological data to try and more quickly identify patterns and correlations between certain physiological variables and target diagnoses. However, even these techniques have flaws and drawbacks that result in unusable and inaccurate results for individuals.

SUMMARY

The term embodiment and like terms are intended to refer broadly to all of the subject matter of this disclosure and the claims below. Statements containing these terms should be understood not to limit the subject matter described herein or to limit the meaning or scope of the claims below. Embodiments of the present disclosure covered herein are defined by the claims below, not this summary. This summary is a high-level overview of various aspects of the disclosure and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this disclosure, any or all drawings and each claim.

Embodiments of the present disclosure include a system, comprising: one or more data processors; and a non-transitory computer-readable storage medium containing instructions which, when executed on the one or more data processors, cause the one or more data processors to perform operations including: accessing a latent space mapping associated with baseline physiological data associated with a subject or a population of subjects, wherein the baseline physiological data is associated with a baseline timeframe, wherein the baseline timeframe is associated with a health condition, wherein the baseline physiological data includes data across a plurality of dimensions in an input space, and wherein the latent space mapping is usable to encode data across the plurality of dimensions into a latent space having fewer dimensions than the plurality of dimensions; accessing query physiological data, wherein the query physiological data is associated with a time outside of the baseline timeframe, and wherein the query physiological data includes data across at least some of the plurality of dimensions; encoding the query physiological data into the latent space using the latent space mapping, wherein encoding the query physiological data into the latent space results in a representation in the latent space associated with the query physiological data; and detecting an anomaly associated with a change in the health condition using the representation in the latent space.

In some cases, detecting the anomaly comprises wherein detecting the anomaly comprises: decoding the representation in the latent space into reconstructed data in the input space using the latent space mapping; and measuring an amount of error between the query physiological data and the reconstructed data. In some cases, detecting the anomaly comprises wherein detecting the anomaly comprises comparing a fit of the representation in the latent space with a point cloud generated by encoding the baseline physiological data into the latent space. In some cases, the operations further comprise: accessing the baseline physiological data; and generating the latent space mapping. In some cases, generating the latent space mapping comprises applying a variational autoencoder or a general adversarial network using the baseline physiological data. In some cases, accessing the baseline physiological data comprises selecting physiological data associated with a parallel variable. In some cases, the operations further comprise generating an inference associated with a change in the parallel variable using the detected anomaly.

Embodiments of the present disclosure include a computer-implemented method, comprising: accessing a latent space mapping associated with baseline physiological data associated with a subject or a population of subjects, wherein the baseline physiological data is associated with a baseline timeframe, wherein the baseline timeframe is associated with a health condition, wherein the baseline physiological data includes data across a plurality of dimensions in an input space, and wherein the latent space mapping is usable to encode data across the plurality of dimensions into a latent space having fewer dimensions than the plurality of dimensions; accessing query physiological data, wherein the query physiological data is associated with a time outside of the baseline timeframe, and wherein the query physiological data includes data across at least some of the plurality of dimensions; encoding the query physiological data into the latent space using the latent space mapping, wherein encoding the query physiological data into the latent space results in a representation in the latent space associated with the query physiological data; and detecting an anomaly associated with a change in the health condition using the representation in the latent space.

In some cases, detecting the anomaly comprises wherein detecting the anomaly comprises: decoding the representation in the latent space into reconstructed data in the input space using the latent space mapping; and measuring an amount of error between the query physiological data and the reconstructed data. In some cases, detecting the anomaly comprises wherein detecting the anomaly comprises comparing a fit of the representation in the latent space with a point cloud generated by encoding the baseline physiological data into the latent space. In some cases, the method further comprises: accessing the baseline physiological data; and generating the latent space mapping. In some cases, generating the latent space mapping comprises applying a variational autoencoder or a general adversarial network using the baseline physiological data. In some cases, accessing the baseline physiological data comprises selecting physiological data associated with a parallel variable. In some cases, the method further comprises generating an inference associated with a change in the parallel variable using the detected anomaly.

Embodiments of the present disclosure include a computer-program product tangibly embodied in a non-transitory machine-readable storage medium, including instructions configured to cause a data processing apparatus to perform operations including: accessing a latent space mapping associated with baseline physiological data associated with a subject or a population of subjects, wherein the baseline physiological data is associated with a baseline timeframe, wherein the baseline timeframe is associated with a health condition, wherein the baseline physiological data includes data across a plurality of dimensions in an input space, and wherein the latent space mapping is usable to encode data across the plurality of dimensions into a latent space having fewer dimensions than the plurality of dimensions; accessing query physiological data, wherein the query physiological data is associated with a time outside of the baseline timeframe, and wherein the query physiological data includes data across at least some of the plurality of dimensions; encoding the query physiological data into the latent space using the latent space mapping, wherein encoding the query physiological data into the latent space results in a representation in the latent space associated with the query physiological data; and detecting an anomaly associated with a change in the health condition using the representation in the latent space.

In some cases, detecting the anomaly comprises wherein detecting the anomaly comprises: decoding the representation in the latent space into reconstructed data in the input space using the latent space mapping; and measuring an amount of error between the query physiological data and the reconstructed data. In some cases, detecting the anomaly comprises wherein detecting the anomaly comprises comparing a fit of the representation in the latent space with a point cloud generated by encoding the baseline physiological data into the latent space. In some cases, the operations further comprise: accessing the baseline physiological data; and generating the latent space mapping. In some cases, generating the latent space mapping comprises applying a variational autoencoder or a general adversarial network using the baseline physiological data. In some cases, accessing the baseline physiological data comprises selecting physiological data associated with a parallel variable. In some cases, the operations further comprise generating an inference associated with a change in the parallel variable using the detected anomaly.

BRIEF DESCRIPTION OF THE DRAWINGS

The specification makes reference to the following appended figures, in which use of like reference numerals in different figures is intended to illustrate like or analogous components.

DETAILED DESCRIPTION

Figure 1:
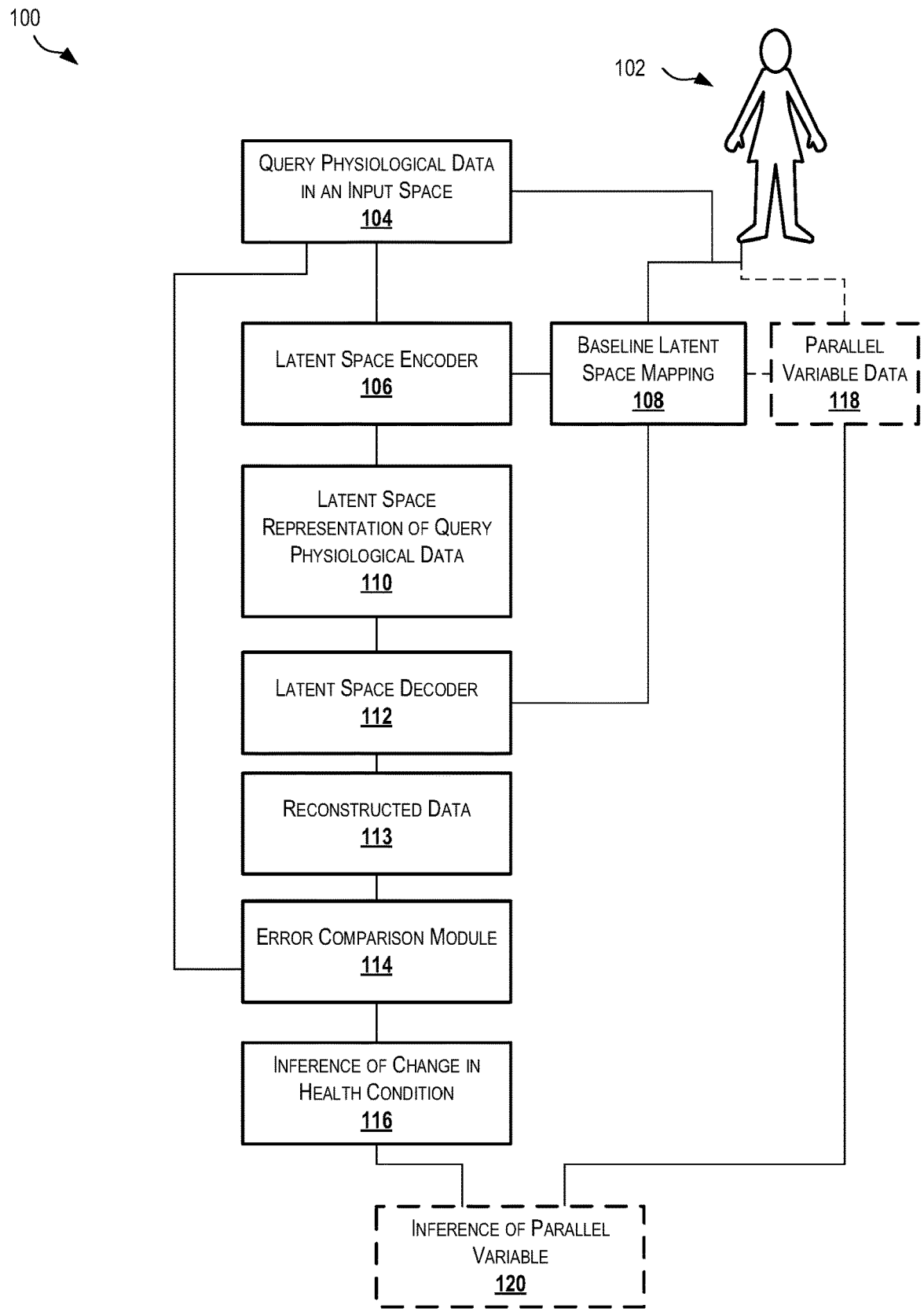
FIG. 1 is an schematic diagram of a health condition detection environment according to certain aspects of the present disclosure.

Certain aspects and features of the present disclosure relate to detecting individual-specific changes in health conditions based on physiological data streams in longitudinal studies. After collecting sufficient physiological data for a baseline timeframe, this baseline physiological data can be de-dimensionalized by modeling the physiological data from an n-dimensional input space into a k-dimensional latent space, where $k<n$. The model can result in a latent space mapping, which can be used to then convert newly collected physiological data into a representation in the latent space (e.g., a point in the latent space). By comparing the representation (e.g., point) in the latent space with the baseline data as seen in the latent space, a determination can be made as to whether the representation fits within the baseline data or is anomalous. In some cases, this determination can include converting the representation back to the input space and computing an error between the original newly collected physiological data and this reconstructed data.

In a longitudinal study, physiological data and other data (e.g., data which may be correlated to the physiological data or to a health condition) can be collected on a single subject (e.g., single individual or patient) over the course of a specific or indefinite timeframe. Since only data associated with the single individual is collected, the longitudinal study is subject-specific. As used herein, the term longitudinal study is inclusive of formal and informal data collection associated with a single individual. In some cases, a longitudinal study of a single subject can be appended or informed by data from a closely related subject, such as a genetic twin or otherwise suitably related subject.

The data in the longitudinal study can be any suitable data, such as physiological data. Physiological data can include any data associated with the life, health, and functionality of a living organism. Physiological data can include individual data points and/or data streams comprising multiple data points, such as sequential data points. Examples of types of physiological data include measurements related to blood pressure, skin conductance, electrocardiograms, electroencephalograms, electromyograms, heart rate, blood oxygenation, weight, height, number of steps taken, activity (e.g., duration and/or intensity of active periods), and other suitable measures. In some cases physiological data can include subjective measurements, such as measurements related to perceived pain, state of mind, and other such measurements. Physiological data can be numerical or categorical in nature, but can be represented in numerical form.

In some cases, physiological data can include measurements related to external factors that impact or are expected to impact a subject's physiology, such as measurements related to medicine intake, ambient weather conditions, stressors (e.g., work, school, tragedy), environment, and the like. In some cases, certain external factors may be included as parallel variable data, as described in further detail herein. In some cases, biological data can be used instead of physiological data for all instances described herein, as appropriate.

Physiological data can include a number of different variables or data streams, each indicative of a different type of measurement. The physiological data can have n different variables. In one example, physiological data containing heart rate information, blood pressure information, electrocardiograph information, and number of steps walked per day can be described as being 4-dimensional, since it contains four different types of measurements or data streams. Any number of dimensions can be used.

Physiological data can be multi-modal in nature and can come from any number of different types of sensors or input devices. In some cases, physiological data can include data that is manually entered (e.g., by a subject or medical professional). Physiological data can include automatically captured data. Physiological data can come in different frequencies, such as high-rate data streams (e.g., a smartwatch continuously measuring movement and heartrate many times over the course of a day) or low-rate data streams (e.g., glucose measurements taken weekly or electrocardiogram measurements taken yearly). To account for different rates of data streams, physiological data can include data from data streams that have been transformed into a waveform of feature vectors at a selected temporal resolution (e.g., every minute, every hour, etc.). In some cases, physiological data can comprise abstracted data. Abstracted data can include data derived from raw data. For example, while a heartrate sensor may generate a waveform indicative of an individual's heart rate, that raw data can be abstracted into a numerical heart rate and/or a measure of heart rate variability.

Physiological data can be collected over a period of time known as a baseline timeframe. The baseline timeframe can be defined in any suitable fashion, such as the period of time before a current time, a preset period of time (e.g., three years), a present number of measurements taken for some or all physiological data, by a parallel variable as described in further detail herein (e.g., a baseline timeframe can be defined as times during which medication is taken or is known to be effecting the subject), by an external variable (e.g., times when the subject is at a physician's office), or in any other suitable way. In some cases, the baseline timeframe can be dynamic, being re-evaluated whenever a latent space mapping is needed. In some cases, however, the baseline timeframe can be static, generating a latent space mapping that can be reused over a period of time.

The physiological data collected over the course of the baseline timeframe can be referred to as baseline physiological data or baseline data. This baseline data can be accessed and converted (e.g., encoded) into a k-dimensional latent space representation of the baseline data. To ensure the baseline data is de-dimensionalized upon conversion into the latent space representation, the k dimensions of the latent space can be fewer than the n dimensions of the baseline data. While the dimensions of the baseline data each refer to measurements or data streams, the dimensions of the latent space are not representative of any specific measurement or data stream, but are instead designed to be representative of patterns and trends within the overall data set. The baseline data can be referred to as being in a n-dimensional input space, whereas the latent space representation of that data can be referred to as being in a k-dimensional latent space. The latent space transformation can be more than a principal component analysis, but can be a non-linear reduction of dimensionality. While the baseline data representation in the latent space can be described as a point in some instances, it may also be described as a region, range, or shape within the latent space in some instances. For example, when the baseline data contains information over a number of time points and number of individuals, the representation of the baseline data in the latent space may be a region of points.

A latent space can be a set of dimensions that is usable to differentiate one or more features associated with a subject or population of subjects. Data from the input space can be mapped onto or projected onto the dimensions of the latent space. Thus, the dimensions of the latent space may not be directly observable, measurable, or collectable for a subject, but are instead determined based on applying a latent space mapping to observed, measured, or collected data. A latent space can be considered a set of dimensionality based off of the measurable dimensions of the physiological data where the ability to distinguish individual data points (e.g., a set of related measurements) in the new latent space is preserved.

The process of converting baseline data from the input space into the latent space can make use of a latent space mapping. The latent space mapping can be generated through any suitable technique, such as any suitable machine learning technique. In some cases, the latent space mapping can be generated through an unsupervised machine learning technique. In some cases, the latent space mapping can be generated through the application of a variational autoencoder (VAE). In some cases, the latent space mapping can be generated through the application of a general adversarial network (GAN). The process of generating the latent space mapping defines the k dimensions of the latent space in terms of the n dimensions of the input space. The process of generating the latent space mapping can be an iterative process involving numerous interim latent space mappings until an optimal, sufficient, and/or desired latent space mapping is achieved.

For example, when a VAE is used, the baseline data is encoded into the latent space, the latent space encoding of the baseline data is decoded back into the input space as reconstructed data, and an error is calculated between this reconstructed data and the original baseline data. The latent space mapping is then adjusted, optionally based on the error data, until the error is minimized or drops below a threshold amount of acceptable error.

In another example, when a GAN is used, a generator model is trained to convert random data into output data that is indistinguishable from baseline data to a discriminator model. The discriminator model is continuously trained to improve and detect differences between the generator model's output data and the actual baseline data, while the generator model is continuously trained to improve and generate more accurate output data that is indistinguishable to the discriminator model. Once the models have been trained sufficiently, the parameters of the generator model can be used to identify parts of the input space useful for anomaly detection. The parameters of the generator model can be used as a latent space mapping to convert baseline data into a latent space.

Once the latent space mapping has been generated, the baseline data can be converted into the latent space and can be represented as a set of points of k dimensions in the latent space. This set of points can be known as a point cloud or a baseline point cloud. Since the latent space mapping is generated from the baseline data from a subject-specific longitudinal study, the latent space mapping is subject-specific.

After a latent space mapping has been generated for baseline data, the latent space mapping can be used to detect anomalous physiological data. Query physiological data can be any physiological data for which an anomalous determination (e.g., detection of a change in health condition) is desired. In some cases, query physiological data can be newly collected data, such as data collected at a physician's office at a time when a detection in change of a health condition is desired. In some cases, however, query physiological data can be old data. The query physiological data can be from a timeframe outside of the baseline timeframe.

Query physiological data can be converted (e.g., encoded) from its n-dimensional input space into the k-dimensional latent space using the latent space mapping generated from the baseline data. This conversion can result in a point or multiple points representative of the query physiological data. This latent space representation of the query physiological data can be used to determine whether the query physiological data is anomalous. In some cases, the latent space representation of the query physiological data (e.g., point in latent space) can be compared to the baseline point cloud to determine if it fits within the baseline point cloud. If it does not fit within the baseline point cloud, an inference can be made that the query physiological data is anomalous.

In some cases, the latent space representation of the query physiological data can be decoded (e.g., reconstructed) from the latent space into the input space. The resultant decoded data can be referred to as reconstructed data. This reconstructed data from the query physiological data can then be compared to the original query physiological data. An inference that the query physiological data is anomalous can be made when the error between the query physiological data and the reconstructed data is greater than a threshold amount. Higher error is indicative that the latent space mapping cannot be used to accurately encode/decode the query physiological data. Since the latent space mapping has been generated to accurately encode/decode baseline physiological data, an inference can be made that the query physiological data, which cannot be accurately encoded/decoded with the same latent space mapping must therefore be anomalous when compared to the baseline data.

Determination of query physiological data as anomalous can be used to identify changes in health conditions. A health condition can be correlated or associated with the baseline physiological data. When query physiological data is determined to be anomalous, it can be indicative that the health condition associated with the baseline physiological data has changed.

In some cases, parallel variable data can be collected as part of or separate from the physiological data. The parallel variable can be any suitable variable that is collected with or alongside the physiological data. Parallel variables can be physiological or non-physiological.

In an example, a parallel variable can be information about the application of medicine, such as minutes since ingestion of a prescription pill. This information can be provided by the subject or can be automatically provided, such as via a smart pillbox (e.g., an internet-of-things device) In this example, the baseline data can be based on physiological data at or after ingestion of the pill. Then, when query physiological data is tested against the latent space mapping, an indication of anomalous data can be indicative that the medicine is wearing off or no longer effecting the subject. This technique can be used to track medication compliance or efficacy, as well as to help determine subject-specific dosing.

In another example, a parallel variable can be information about a potential stressor, such as a subject's location information (e.g., at work, at school, etc.). In this example, the latent space mapping itself or subsequent determinations of anomalous query physiological data can be used to identify patterns associated with the parallel variable. For example, a latent space mapping can be made based on a baseline timeframe including times when an individual is self-diagnosed as being non-depressed. If query physiological data associated with being at work or school is often determined to be anomalous, it may be indicative of work or school being a trigger for a change in a mental health condition.

In some cases, detection of anomalies in query physiological data over time can be used to adjust the baseline timeframe for generating an updated latent space mapping. For example, if more than a threshold number of anomalies are detected in query physiological data over a preset period of time, it can be indicative that the latent space mapping should be updated, and thus the baseline timeframe can be adjusted, such as to include some of the past query physiological data, and even some of the past query physiological data that had previously been considered anomalous. In some cases, if more than a threshold amount of anomalies are identified in query physiological data, a prompt can be given to look into whether or not the anomalies are actually indicative of a change in health condition, or not. This further investigation can be conducted by the subject or by a medical professional, although that need not always be the case. If it is determined that a change in health condition has not occurred, the latent space mapping can be updated by updating the baseline timeframe.

Certain aspects and features of the present disclosure can be especially useful for diagnosing diseases or conditions that have long-term changes and/or for which strong indicators have not yet been identified. Certain aspects and features of the present disclosure can also be especially useful for diagnosing diseases or conditions that rarely show symptoms. For example, subjects suffering from epilepsy may only have occasional seizures, such as once or a few times per year. However, by using presence of an epileptic seizure as a parallel variable, a subject may be able to identify when anomalous query physiological data is occurring prior to an actual epileptic seizure occurring. For example, if a latent space mapping is trained on physiological data containing encephalographic data such that query physiological data associated with occurrences of seizures is identified as anomalous, a future query physiological data that is identified as anomalous can be indicative of a possible oncoming seizure, and thus provide advance warning to the subject, allowing that subject to seek medical attention and/or avoid dangerous activities (e.g., driving a car).

In some cases, baseline data and latent space mappings can be selected and trained such that an indication of anomalous query physiological data is indicative of a undesired change in health condition (e.g., presence of a seizure in an otherwise healthy individual). However, in some cases, the baseline data and latent space mappings can be selected and trained contrarily such that indication of anomalous query physiological data is indicative of no change in health condition or a positive change (e.g., a change from a negative health condition, such as an indication of not having a seizure).

Certain aspects of the present disclosure can be leveraged to provide real-time, near real-time, or occasional indications and warnings to an individual. Certain aspects of the present disclosure can be performed automatically and/or periodically based on incoming data from a myriad of sources (e.g., internet of things devices, internet-connected devices, smartphones, smart watches, manual equipment, medical professional databases, etc.). Certain aspects of the present disclosure can provide and/or enable personalized healthcare that is tailored to a specific subject. Certain aspects of the present disclosure can easily and quickly handle large amounts of data and data from multi-modal data streams. In some cases, certain aspects of the present disclosure can handle unlabeled data (e.g., data not labeled as being anomalous) and still leverage the unlabeled data to determine whether query physiological data is anomalous.

Certain aspects of the present disclosure can operate more efficiently than other anomaly detection techniques. For example, anomaly detection using standard machine learning techniques can be very difficult when large amounts of data are being used. Some solutions attempt to increase the training dataset, but without more anomaly examples and more diversity of actual anomalies, standard machine learning approaches cannot solve such problems. However, the use of latent spaces, such as described herein, help solve the issue by removing irrelevant data. As an example, finding an anomaly can be analogized by finding a needle in a haystack. While a standard machine learning technique may try to improve detection by increasing the overall size of the haystack to provide m more training, certain aspects of the instant applicant instead are able to effectively throw away irrelevant hay from the haystack.

In some cases, certain aspects of the present disclosure can be especially useful in determining an anomaly associated with a subject (e.g., an individual). However, in some cases, aspects of the present disclosure can be associated with a population of subjects instead of a single subject. For example, a population of subjects can include subjects that share a common similarity, such as subjects from the same geographical location, subjects with a particular disease, subjects of the same age or similar ages, subjects of the same gender, subjects sharing a familial relationship, and others.

These illustrative examples are given to introduce the reader to the general subject matter discussed here and are not intended to limit the scope of the disclosed concepts. The following sections describe various additional features and examples with reference to the drawings in which like numerals indicate like elements, and directional descriptions are used to describe the illustrative embodiments but, like the illustrative embodiments, should not be used to limit the present disclosure. The elements included in the illustrations herein may not be drawn to scale.

FIG. 1 is an schematic diagram of a health condition detection environment 100 according to certain aspects of the present disclosure. The environment 100 can be associated with a subject 102, such as a human individual. Over the course of a baseline timeframe, physiological data can be collected for the individual and be used to generate a baseline latent space mapping 108. The baseline latent space mapping 108 can be based on historical physiological data that falls within the bounds of the baseline timeframe. The baseline timeframe can be contiguous or non-contiguous. The baseline latent space mapping 108 can be generated through unsupervised machine learning and can be used to generated a k-dimensional latent space representation of the n-dimensional baseline physiological data, where k<n. In some cases, parallel variable data 118 can be collected. The parallel variable data 118 can be collected alongside the baseline physiological data, although that need not always be the case. The parallel variable data 118 can be based on the subject 102, although that need not always be the case.

The environment can include query physiological data 104 associated with the subject 102 that has been collected. The query physiological data 104 can be in an n-dimensional input space, and can include some or all of the same data streams that make up the baseline physiological data used to generate the baseline latent space mapping 108.

The query physiological data 104 can be passed through a latent space encoder 106, which makes use of the baseline latent space mapping 108 to encode the query physiological data 104 into a latent space representation of the query physiological data 110. The latent space representation of the query physiological data 110 can be decoded back into the input space as reconstructed data 113 by a latent space decoder 112 making use of the baseline latent space mapping 108. Once decoded, the resultant reconstructed data 113 can be compared to the query physiological data 104 by an error comparison module 114. The error comparison module 114 can determine an amount of error between the query physiological data 104 and the reconstructed data 113. Based on that amount of error, an inference of a change in a health condition 116 can be made. For example, a high amount of error (e.g., above a threshold amount) can be indicative that a change in health condition has occurred, and the inference of the change in health condition 116 can be positive.

In some cases, an inference of the parallel variable 120 can be made using the parallel variable data 118 and the inference of a change in health condition 118. For example, in a parallel variable associated with taking medication, the parallel variable data 118 may be used to inform the baseline time frame, and thus to facilitate generation of the baseline latent space mapping 108. Then, a positive inference of a change in health condition 116 can lead to a positive inference of a change in the parallel variable 120, such as an inference that the medication has worn off or was not taken.

Figure 2:
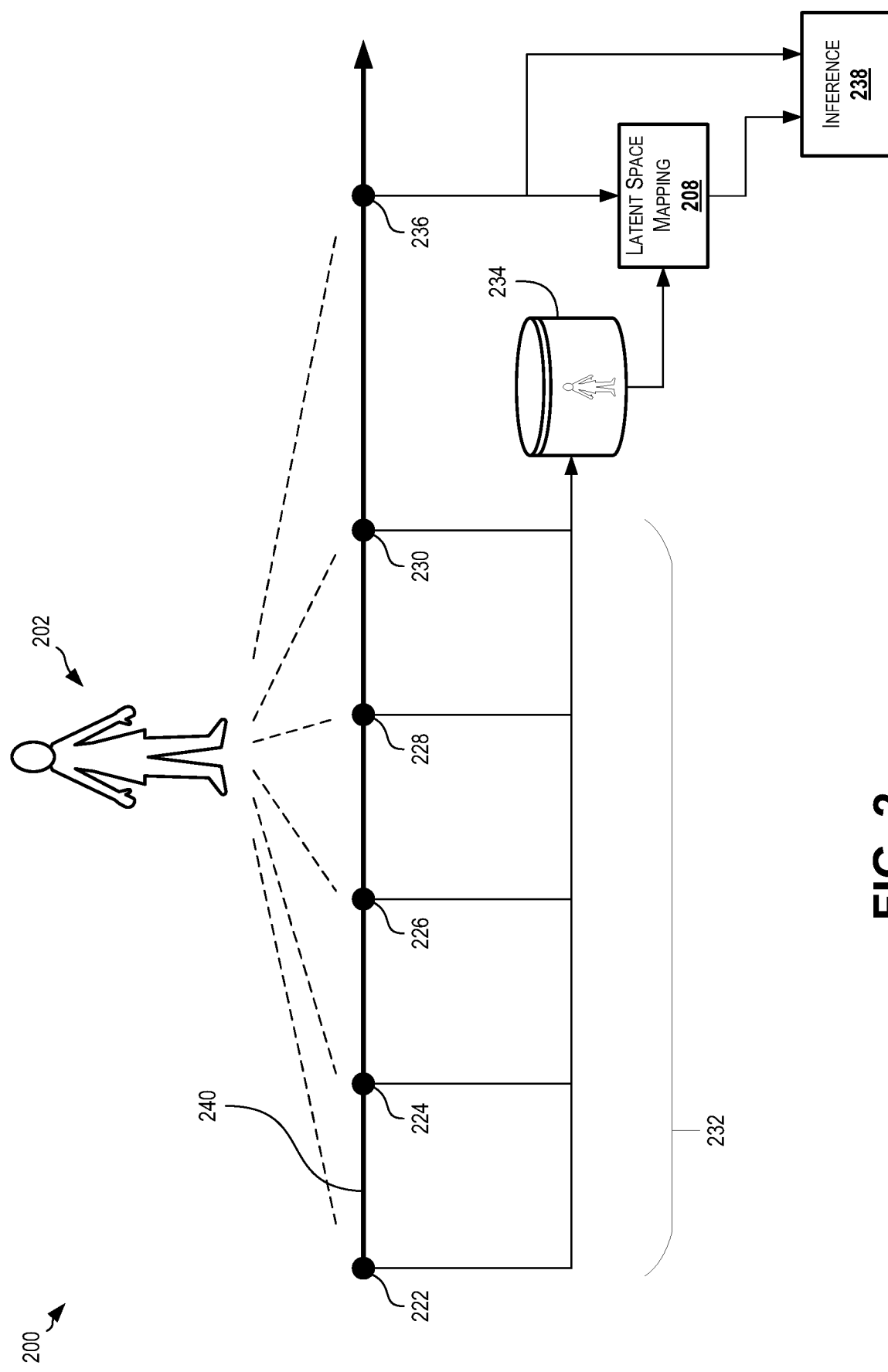
FIG. 2 is a schematic diagram of a longitudinal study used to build and leverage a latent space mapping to generate an inference related to a change in a health condition according to certain aspects of the present disclosure.

FIG. 2 is a schematic diagram of a longitudinal study 200 used to build and leverage a latent space mapping 208 to generate an inference 238 related to a change in a health condition according to certain aspects of the present disclosure. The longitudinal study 200 can relate to a single subject 202. Timeline 240 is representative of a timeframe with a beginning and an indefinite end. The timeline 240 contains numerous instances 222, 224, 226, 228, 230, 236 associated with collection of physiological data. Physiological data can include data from n different data streams (e.g., data sources). Instances 222, 224, 226, 228, 230, 236 need not be equally spaced and need not involve the collection of all of the same data streams.

Baseline physiological data 234 can be collected from instances 222, 224, 226, 228, 230 that fall within a baseline timeframe 232. Depending on the size of the baseline timeframe 232, fewer or more instance may be used as the baseline physiological data 234. The baseline physiological data 234 can be used to generate a latent space mapping 208.

Physiological data from an instance 236 outside of the baseline timeframe 232 can be used as query physiological data. This query physiological data can be used with the latent space mapping 208 from the baseline physiological data 234 to generate an inference 238. The latent space mapping 208 can be applied to the query physiological data to transform (e.g., encode/decode) the query physiological data from an input space into a latent space and then back from the latent space into the input space as reconstructed data. The inference 238 can be based on a comparison of reconstructed data with the query physiological data. If the reconstructed data closely matches the query physiological data, no inference may be generated or a negative inference may be generated. However, if the reconstructed data does not closely match the query physiological data (e.g., above a threshold amount of error), an inference can be generated that the query physiological data is anomalous, and thus a change in health condition has occurred.

Figure 3:
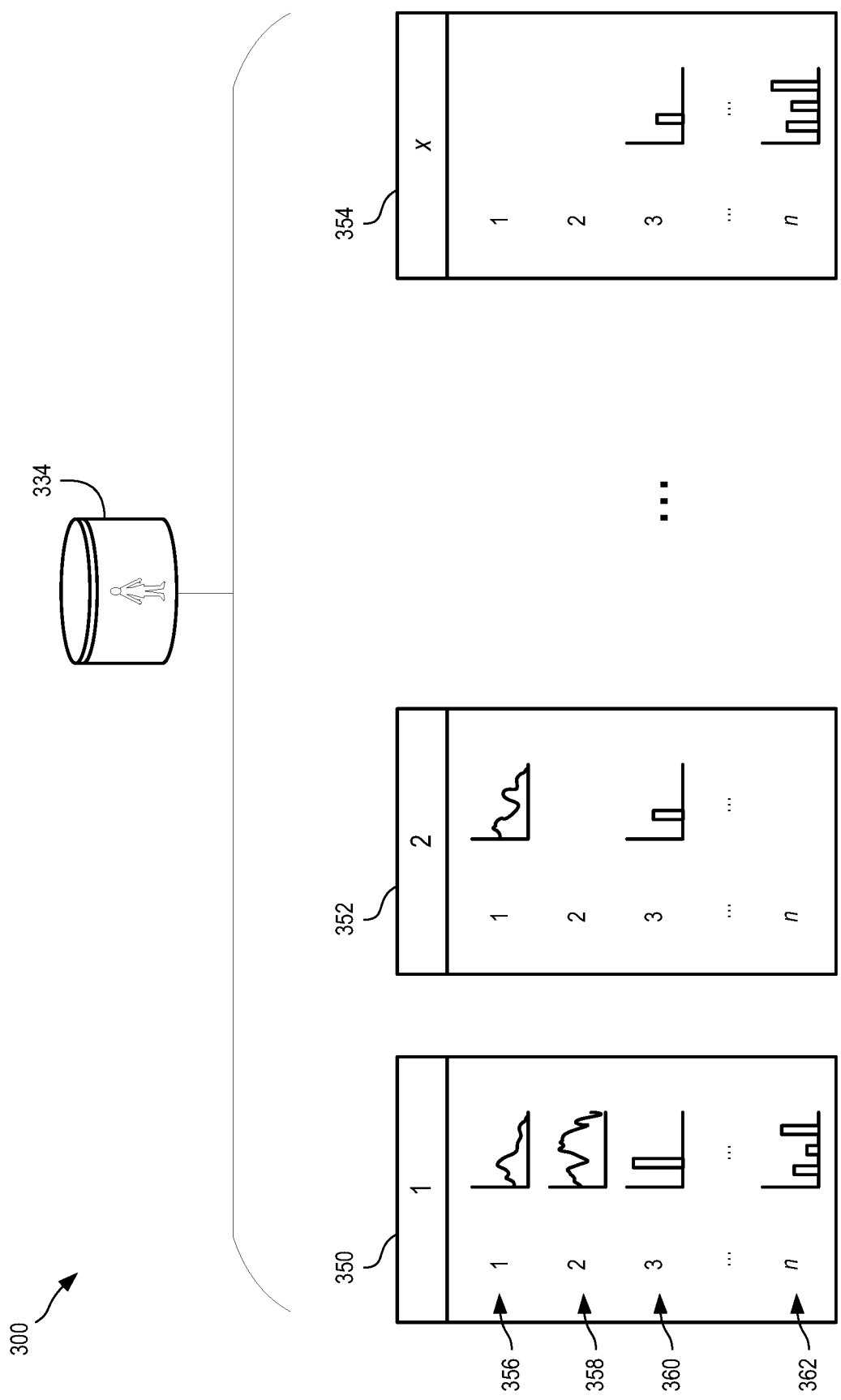
FIG. 3 is a schematic diagram of a collection of physiological data associated with a subject according to certain aspects of the present disclosure.

FIG. 3 is a schematic diagram of a collection 300 of physiological data associated with a subject according to certain aspects of the present disclosure. The collection 300 comprises a data store 334 of baseline physiological data comprising a set of x different data points 350, 352, 354. While x can be one or more, the baseline physiological data often contains numerous data points. While the collection 300 described in FIG. 3 is one technique for interpreting and organizing physiological data, physiological data can be organized in other ways.

Each data point 350, 352, 354 can include n different data streams 356, 358, 360, 362 (e.g., data sources). Each data stream 356, 358, 360, 362 can include one or more data points associated with the subject. In some cases, each data point 350, 352, 354 of the data store 334 may include data for each of the data streams 356, 358, 360, 362, although that need not always be the case. In some cases, such as depicted in collection 300, some data points 350, 352, 354 of the data store 334 may include for fewer than all of the data streams 356, 358, 360, 362. In an example, a first data point 350 may comprise data for data streams 356, 358, 360, 362; a second data point 352 may comprise data for data streams 356, 360; and an nth data point 354 may comprise data for data streams 360, 362.

Figure 4:
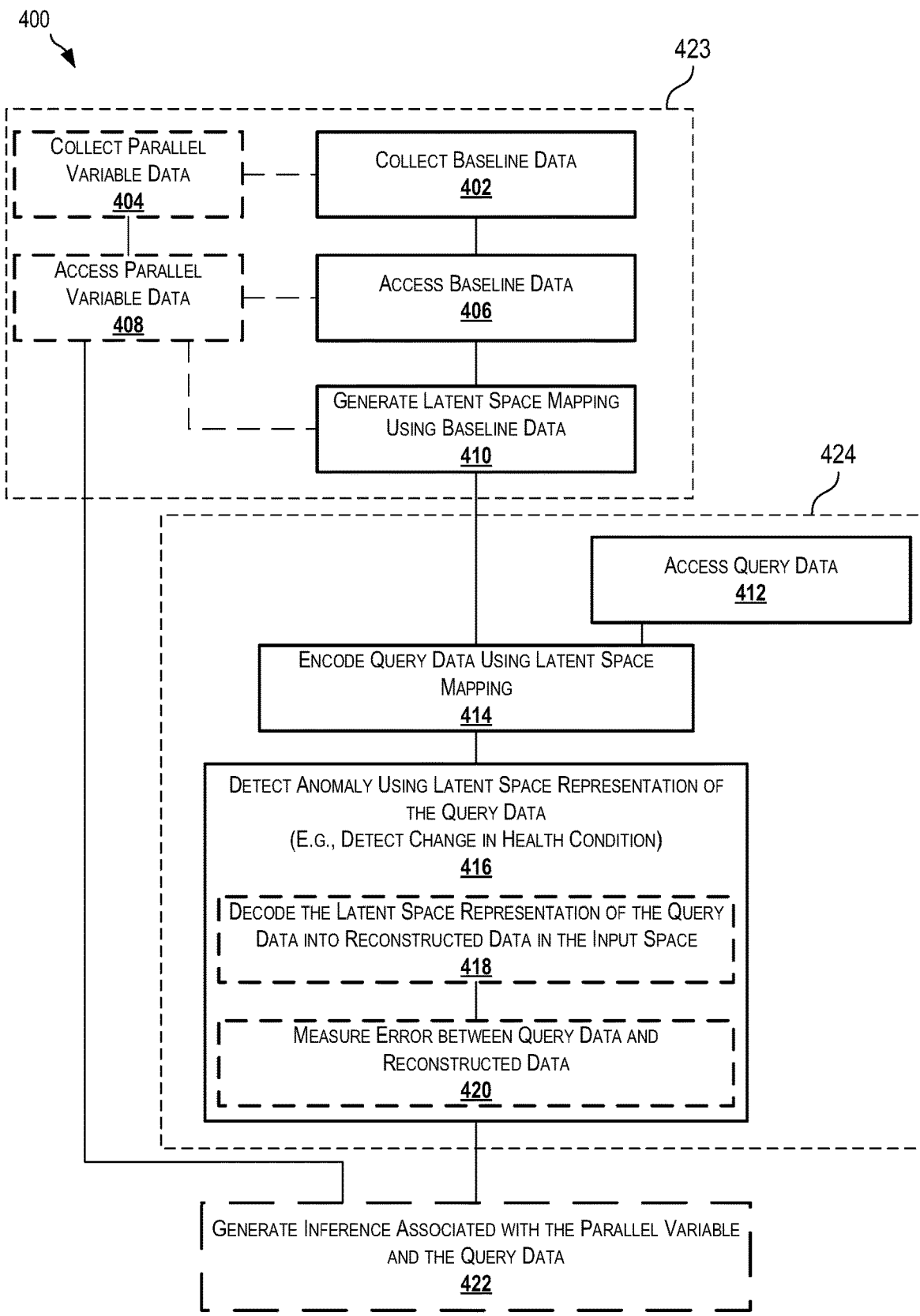
FIG. 4 is a process for building and leveraging a latent space mapping to detect a change in a health condition according to certain aspects of the present disclosure.

FIG. 4 is a process 400 for building and leveraging a latent space mapping to detect a change in a health condition according to certain aspects of the present disclosure. At block 402, baseline data (e.g., baseline physiological data) can be collected. Baseline data can be collected in any suitable manner and in any suitable form. In an example, baseline data can be collected from a combination of any number of sensors, input devices, and/or data stores. Baseline data can be the collection 300 of physiological data of FIG. 3. At block 406, the collected baseline data can be accessed.

In some cases, parallel variable data can be optionally collected at block 404. In some cases, collecting parallel variable data can be intertwined with or separate from collecting baseline data at block 402. In some cases, parallel variable data can be optionally accessed at block 408. In some cases, accessing parallel variable data can be intertwined with or separate from accessing baseline data at block 406.

In some cases, collecting baseline data at block 402 and/or accessing baseline data at block 406 can be based in part on a defined baseline timeline. The baseline timeline can be preset, automatically generated, and/or updated by user input as described herein. In some cases, the baseline timeline can be defined based on parallel variable data, such as parallel variable data that is collected at block 404 or accessed at block 408, as described herein.

At block 410, a latent space mapping can be generated using the baseline data from block 406. The latent space mapping can be generated by applying a machine learning algorithm to the baseline data to de-dimensionalize the baseline data into a fewer number of dimensions. The machine learning algorithm can be an unsupervised machine learning algorithm, such as a variable autoencoder (VAE) or a global adversarial network (GAN). Generating the latent space mapping at block 410 can comprise training a model used to encode the baseline data from an n-dimensional input space into a k-dimensional latent space, where k<n. In some cases, generating a latent space mapping at block 410 can comprise using parallel variable data from block 408.

Blocks 402, 406, 410 and optional blocks 404, 408 can define a process 423 of generating a latent space mapping form physiological data. After a latent space mapping has been generated, process 424 can be used to detect anomalous data and/or generate an inference based on input data (e.g., query data) from outside of the baseline timeline.

At block 412, query data can be accessed. The query data can comprise physiological data that is not included in the baseline data (e.g., outside of the baseline timeframe). For example, query data can include data collected as part of a medical examination such that a determination about whether a change in a health condition has occurred can be made and interpreted by a medical professional. In another example, query data can include incoming data from peripheral devices used by a subject so that an indication of a change in a health condition can be determined and presented to the subject, such as in the form of an advanced warning.

At block 414, the query data can be encoded from the n-dimensional input space into the k-dimensional latent space using the latent space mapping from block 410. Encoding the query data can result in a set of one or more points in the latent space representative of the query data.

At block 416, an anomaly can be detected using the latent space representation of the query data. Detecting an anomaly at block 416 can involve making a determination as to whether or not the query data is anomalous when compared to the baseline data. Detecting an anomaly at block 416 can involve detecting a change in a health condition or can involve generating an inference that a change in a health condition has occurred.

Detecting the anomaly at block 416 can be performed in any suitable technique. In some cases detecting an anomaly at block 416 can include comparing the latent space representation of the query data (e.g., a point or multiple points in the latent space) with a latent space representation of the baseline data (e.g., a set of points, such as a point cloud, in the latent space). For example, a latent space representation of the baseline data may define an enclosed area and anomalous latent space representations of the query data may appear as points outside of that enclosed area.

In some cases, however, detecting the anomaly at block 416 can comprise decoding the latent space representation of the query data back into the input space as reconstructed data at block 418. The reconstructed data can be n-dimensional data associated with the same data streams as the baseline physiological data and/or the query data. At block 420, the reconstructed data can be compared to the query data to measure an amount of error. The amount of error measured can be in any suitable format. Error can be measured per dimension (e.g., per data stream), as a combination of error measurements, or otherwise. In some cases, error can be defined based on the difference between a function of the query data and a function of the reconstructed data. In some cases, error can be measured using variances of the query data and the reconstructed data.

Based on the measured error at block 420, a determination can be made as to whether or not the query data is anomalous when compared to the baseline data. This determination can be made based on the error measured at block 420 exceeding a threshold amount. In some cases, this determination can be a generated inference that the query data is anomalous.

In some cases, an inference can be generated at block 422 associated with the parallel variable and the query data. Generating the inference associated with the parallel variable and the query data at block 422 can include using the parallel variable data from block 408 and the detected anomaly from block 416. If an anomaly is detected at block 416 in correlation with a change in a parallel variable, an inference can be made that the presence of the inference may be related or correlated with the presence of the detected anomaly (e.g., a change in the health condition).

Figure 5:
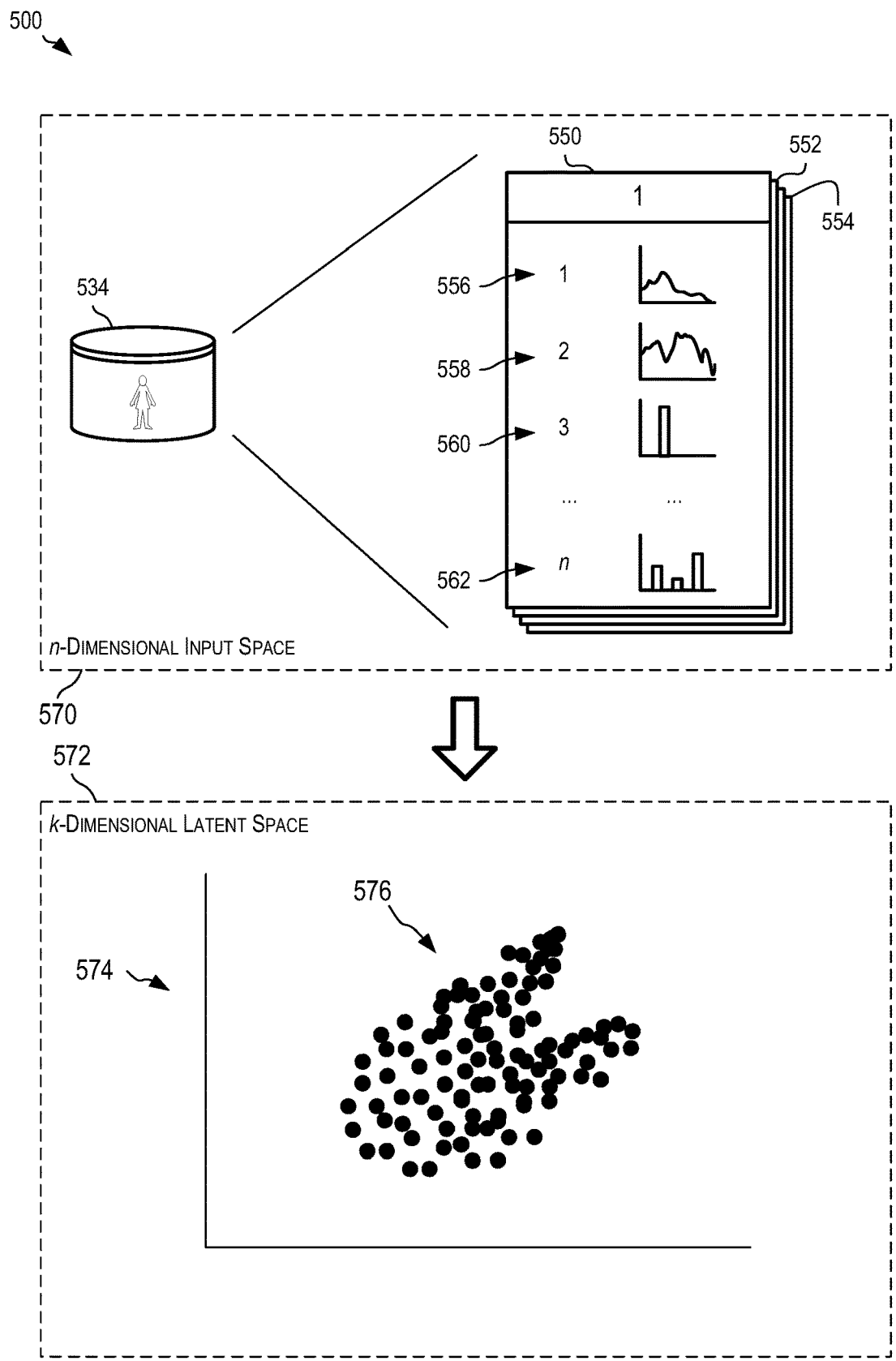
FIG. 5 is a schematic diagram depicting historical physiological data in an input space and the same data mapped into a representation of a latent space according to certain aspects of the present disclosure.

FIG. 5 is a schematic diagram 500 depicting baseline physiological data 534 in an input space 570 and the same data mapped into a representation 576 in a latent space 572 according to certain aspects of the present disclosure. The baseline physiological data 534 can comprise data from multiple data points 550, 552, 554, each of which can contain data associated with n different data streams 556, 558, 560, 562 (e.g., data sources). This baseline physiological data 534 can be presented in an n-dimensional input space 570.

When this baseline physiological data 534 is encoded into a k-dimensional latent space 572, the baseline physiological data 534 can be stored as a representation 576 of the baseline physiological data 534 in the latent space 572. In FIG. 5, the representation 576 is depicted on a two-dimensional chart 574 for illustrative purposes, although the actual representation 576 may comprise a set of k-dimensional points.

Figure 6:
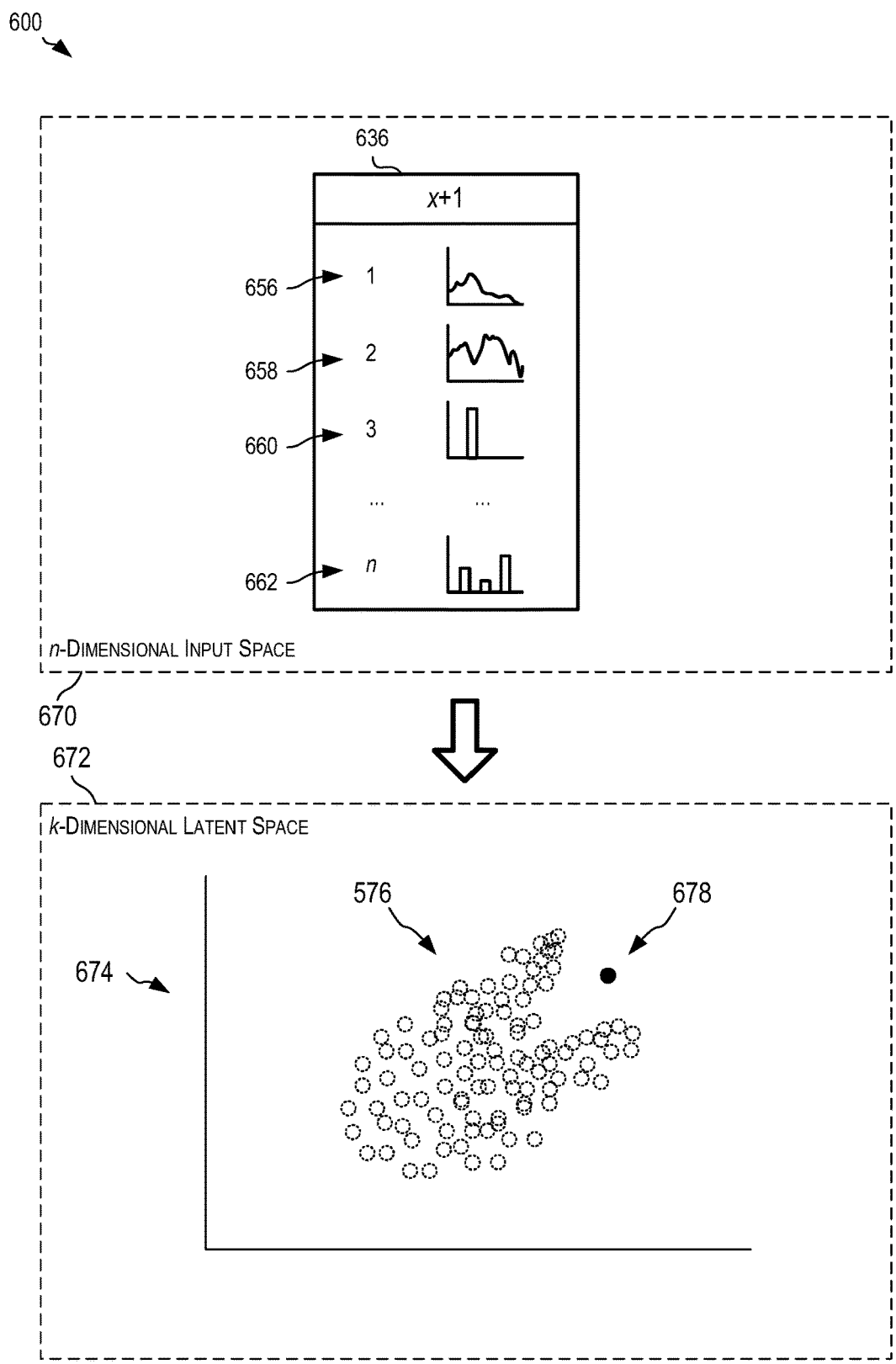
FIG. 6 is a schematic diagram depicting query physiological data in an input space and the same data mapped into a representation of a latent space according to certain aspects of the present disclosure.

FIG. 6 is a schematic diagram 600 depicting query physiological data 636 in an input space 670 and the same data mapped into a representation 678 in a latent space 672 according to certain aspects of the present disclosure. The query physiological data 636 can comprise data from one or more data points, each of which can contain data associated with n different data streams 656, 658, 660, 662 (e.g., data sources), although the query physiological data 636 can comprise fewer than n different data streams. The query physiological data 636 can be presented in an n-dimensional input space 670. The n-dimensional input space 670 can be the same n-dimensional input space 570 of FIG. 5. The query physiological data 636 can be associated with the same subject as the historical physiological data 534 of FIG. 5.

When this query physiological data 636 is encoded into a k-dimensional latent space 672, the query physiological data 636 can be stored as a representation 678 of the query physiological data 636 in the latent space 672. In FIG. 6, the representation 678 is depicted on a two-dimensional chart 674 for illustrative purposes, although the actual representation 678 may comprise a set of k-dimensional points.

Also depicted in FIG. 6 for illustrative purposes is the representation 576 of the baseline physiological data 534 of FIG. 5, shown as dotted circles. As depicted in FIG. 6, the representation 678 of the query physiological data 636 is seen as falling outside of the boundary of the representation 576 of the baseline physiological data 534. In some cases, query physiological data 636 can be identified as anomalous when its representation 678 falls outside of the bounds of the representation 576 of the baseline physiological data 535 in the latent space 672. However, in some cases, no direct comparison between the representation 576 of the baseline physiological data 535 and the representation 678 of the query physiological data 638 is made in order to determine an inference of the query physiological data 638 being anomalous.

Figure 7:
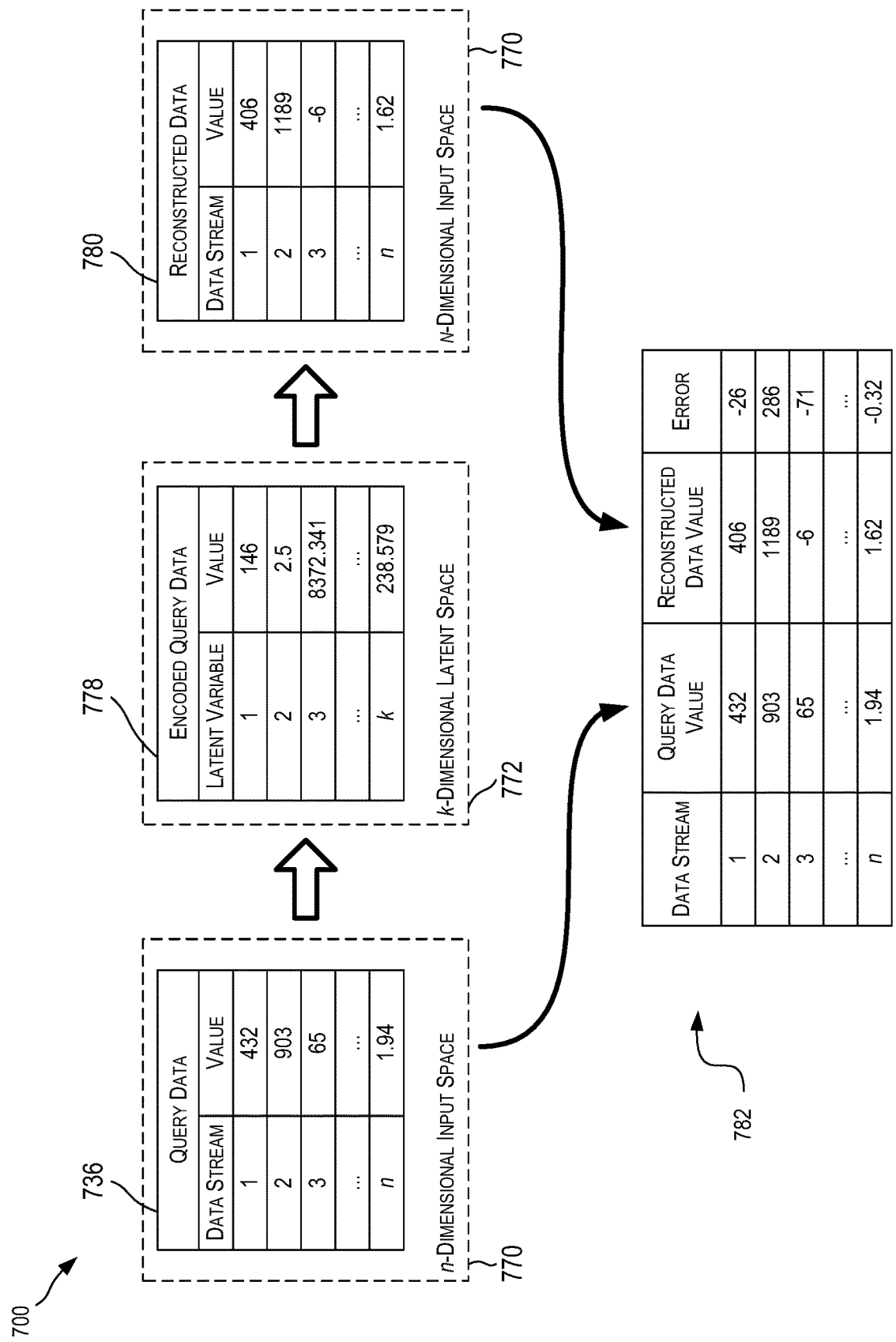
FIG. 7 is a schematic diagram depicting query data in an input space, the resultant encoded query data in the latent space, and reconstructed data in the input space that has been reconstructed from the encoded query data from the latent space according to certain aspects of the present disclosure.

FIG. 7 is a schematic diagram 700 depicting query data 736 in an input space 770, the resultant encoded query data 778 in the latent space 772, and reconstructed data 780 in the input space 770 that has been reconstructed from the encoded query data 778 from the latent space 772 according to certain aspects of the present disclosure. The query data 736 can be query physiological data, such as query physiological data 636 of FIG. 6, presented in an n-dimensional input space 770. Using a latent space mapping created from baseline data associated with the same subject as the query data 778, the query data 778 can be encoded into encoded query data 778 in a k-dimensional latent space 772. Using the same latent space mapping, the encoded query data 778 can be decoded back into the n-dimensional input space 770 as reconstructed data 780.

If the query data 736 perfectly fits the baseline data, it can be presumed that the latent space mapping based on that baseline data that is used to encode the query data 736 can be used to decode the resultant encoded query data 778 into reconstructed data 780 with little to no difference in the values between the query data 736 and the reconstructed data 780. However, if there is more than a threshold amount of error between the query data 736 and the reconstructed data 780, an inference can be made that the query data 736 does not fit well with the baseline data, and is thus considered anomalous.

An example of an error calculation is depicted in chart 782, showing a difference between query data values and reconstructed data values. However, other techniques for determining error between the query data 736 and the reconstructed data 780 can be used.

Figure 8:
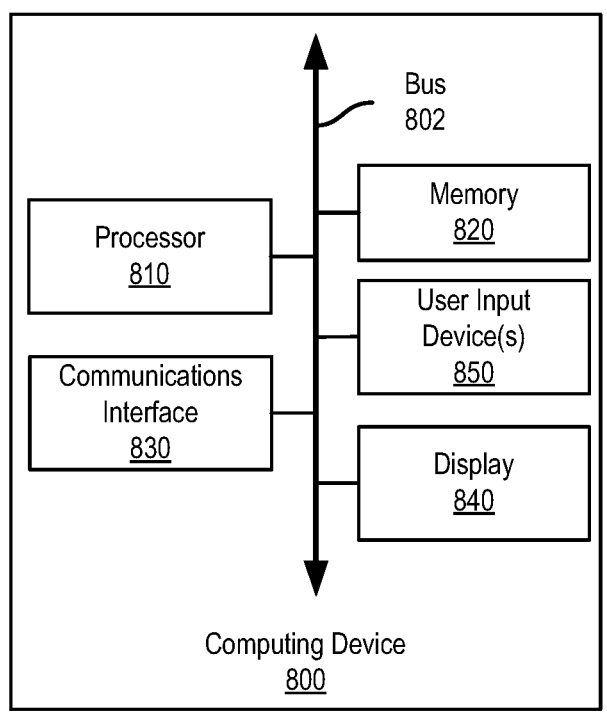
FIG. 8 is a schematic diagram depicting an example computing device suitable for use in example systems or methods or processes for determining a change in health condition according to certain aspects of the present disclosure.

FIG. 8 is a schematic diagram depicting an example computing device 800 suitable for use in example systems or methods or processes for determining a change in health condition according to certain aspects of the present disclosure. The example computing device 800 includes a processor 810 which is in communication with the memory 820 and other components of the computing device 800 using one or more communications buses 802. The processor 810 is configured to execute processor-executable instructions stored in the memory 820 to perform one or more methods or processes as described herein, such as part or all of the example process 400 described above with reference to FIG. 4. The computing device, in this example, also includes one or more user input devices 850, such as a keyboard, mouse, touchscreen, microphone, etc., to accept user input. The computing device 800 also includes a display 840 to provide visual output to a user. In some cases, a computing device can have more or fewer components.

The computing device 800 also includes a communications interface 840. In some examples, the communications interface 830 may enable communications using one or more networks, including a local area network ("LAN"); wide area network ("WAN"), such as the Internet; metropolitan area network ("MAN"); point-to-point or peer-to-peer connection; etc. Communication with other devices may be accomplished using any suitable networking protocol. For example, one suitable networking protocol may include the Internet Protocol ("IP"), Transmission Control Protocol ("TCP"), User Datagram Protocol ("UDP"), or combinations thereof, such as TCP/IP or UDP/IP.

While some examples of methods and systems herein are described in terms of software executing on various machines, the methods and systems may also be implemented as specifically-configured hardware, such as field-programmable gate array (FPGA) specifically to execute the various methods. For example, examples can be implemented in digital electronic circuitry, or in computer hardware, firmware, software, or in a combination thereof In one example, a device may include a processor or processors. The processor comprises a computer-readable medium, such as a random access memory (RAM) coupled to the processor. The processor executes computer-executable program instructions stored in memory, such as executing one or more computer programs. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example computer-readable storage media, that may store instructions that, when executed by the processor, can cause the processor to perform the steps described herein as carried out, or assisted, by a processor. Examples of computer-readable media may include, but are not limited to, an electronic, optical, magnetic, or other storage device capable of providing a processor, such as the processor in a web server, with computer-readable instructions. Other examples of media comprise, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures. The processor may comprise code for carrying out one or more of the methods or processes (or parts of methods or processes) described herein.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation, as appropriate.

The foregoing description of the embodiments, including illustrated embodiments, has been presented only for the purpose of illustration and description and is not intended to be exhaustive or limiting to the precise forms disclosed. Numerous modifications, adaptations, and uses thereof will be apparent to those skilled in the art.

As used below, any reference to a series of examples is to be understood as a reference to each of those examples disjunctively (e.g., "Examples 1-4" is to be understood as "Examples 1, 2, 3, or 4").

Example 1 is a system, comprising: one or more data processors; and a non-transitory computer-readable storage medium containing instructions which, when executed on the one or more data processors, cause the one or more data processors to perform operations including: accessing a latent space mapping associated with baseline physiological data associated with a subject or a population of subjects, wherein the baseline physiological data is associated with a baseline timeframe, wherein the baseline timeframe is associated with a health condition, wherein the baseline physiological data includes data across a plurality of dimensions in an input space, and wherein the latent space mapping is usable to encode data across the plurality of dimensions into a latent space having fewer dimensions than the plurality of dimensions; accessing query physiological data, wherein the query physiological data is associated with a time outside of the baseline timeframe, and wherein the query physiological data includes data across at least some of the plurality of dimensions; encoding the query physiological data into the latent space using the latent space mapping, wherein encoding the query physiological data into the latent space results in a representation in the latent space associated with the query physiological data; and detecting an anomaly associated with a change in the health condition using the point in the latent space. In some cases, the baseline physiological data can be associated with a single subject. In some cases, the latent space comprises a set of dimensions usable to differentiate one or more features associated with the subject or the population of subjects.

Example 2 is the system of example(s) 1, wherein detecting the anomaly comprises wherein detecting the anomaly comprises: decoding the representation in the latent space into reconstructed data in the input space using the latent space mapping; and measuring an amount of error between the query physiological data and the reconstructed data.

Example 3 is the system of example(s) 1, wherein detecting the anomaly comprises wherein detecting the anomaly comprises comparing a fit of the representation in the latent space with a point cloud generated by encoding the baseline physiological data into the latent space.

Example 4 is the system of example(s) 1-3, wherein the operations further comprise: accessing the baseline physiological data; and generating the latent space mapping.

Example 5 is the system of example(s) 4, wherein generating the latent space mapping comprises applying a variational autoencoder or a general adversarial network using the baseline physiological data.

Example 6 is the system of example(s) 4 or 5, wherein accessing the baseline physiological data comprises selecting physiological data associated with a parallel variable.

Example 7 is the system of example(s) 6, wherein the operations further comprise generating an inference associated with a change in the parallel variable using the detected anomaly.

Example 8 is a computer-implemented method, comprising: accessing a latent space mapping associated with baseline physiological data associated with a subject or a population of subjects, wherein the baseline physiological data is associated with a baseline timeframe, wherein the baseline timeframe is associated with a health condition, wherein the baseline physiological data includes data across a plurality of dimensions in an input space, and wherein the latent space mapping is usable to encode data across the plurality of dimensions into a latent space having fewer dimensions than the plurality of dimensions; accessing query physiological data, wherein the query physiological data is associated with a time outside of the baseline timeframe, and wherein the query physiological data includes data across at least some of the plurality of dimensions; encoding the query physiological data into the latent space using the latent space mapping, wherein encoding the query physiological data into the latent space results in a representation in the latent space associated with the query physiological data; and detecting an anomaly associated with a change in the health condition using the representation in the latent space. In some cases, the baseline physiological data can be associated with a single subject. In some cases, the latent space comprises a set of dimensions usable to differentiate one or more features associated with the subject or the population of subjects.

Example 9 is the method of example(s) 8, wherein detecting the anomaly comprises wherein detecting the anomaly comprises: decoding the representation in the latent space into reconstructed data in the input space using the latent space mapping; and measuring an amount of error between the query physiological data and the reconstructed data.

Example 10 is the method of example(s) 8, wherein detecting the anomaly comprises wherein detecting the anomaly comprises comparing a fit of the representation in the latent space with a point cloud generated by encoding the baseline physiological data into the latent space.

Example 11 is the method of example(s) 8-10, further comprising: accessing the baseline physiological data; and generating the latent space mapping.

Example 12 is the method of example(s) 11, wherein generating the latent space mapping comprises applying a variational autoencoder or a general adversarial network using the baseline physiological data.

Example 13 is the method of example(s) 11 or 12, wherein accessing the baseline physiological data comprises selecting physiological data associated with a parallel variable.

Example 14 is the method of example(s) 13, further comprising generating an inference associated with a change in the parallel variable using the detected anomaly.

Example 15 is a computer-program product tangibly embodied in a non-transitory machine-readable storage medium, including instructions configured to cause a data processing apparatus to perform operations including: accessing a latent space mapping associated with baseline physiological data associated with a subject or a population of subjects, wherein the baseline physiological data is associated with a baseline timeframe, wherein the baseline timeframe is associated with a health condition, wherein the baseline physiological data includes data across a plurality of dimensions in an input space, and wherein the latent space mapping is usable to encode data across the plurality of dimensions into a latent space having fewer dimensions than the plurality of dimensions; accessing query physiological data, wherein the query physiological data is associated with a time outside of the baseline timeframe, and wherein the query physiological data includes data across at least some of the plurality of dimensions; encoding the query physiological data into the latent space using the latent space mapping, wherein encoding the query physiological data into the latent space results in a representation in the latent space associated with the query physiological data; and detecting an anomaly associated with a change in the health condition using the representation in the latent space. In some cases, the baseline physiological data can be associated with a single subject. In some cases, the latent space comprises a set of dimensions usable to differentiate one or more features associated with the subject or the population of subjects.

Example 16 is the computer-program product of example(s) 15, wherein detecting the anomaly comprises wherein detecting the anomaly comprises: decoding the representation in the latent space into reconstructed data in the input space using the latent space mapping; and measuring an amount of error between the query physiological data and the reconstructed data.

Example 17 is the computer-program product of example(s) 15, wherein detecting the anomaly comprises wherein detecting the anomaly comprises comparing a fit of the representation in the latent space with a point cloud generated by encoding the baseline physiological data into the latent space.

Example 18 is the computer-program product of example(s) 15-17, wherein the operations further comprise: accessing the baseline physiological data; and generating the latent space mapping.

Example 19 is the computer-program product of example(s) 18, wherein generating the latent space mapping comprises applying a variational autoencoder or a general adversarial network using the baseline physiological data.

Example 20 is the computer-program product of example(s) 18 or 19, wherein accessing the baseline physiological data comprises selecting physiological data associated with a parallel variable.

Example 21 is the computer-program product of example(s) 20, wherein the operations further comprise generating an inference associated with a change in the parallel variable using the detected anomaly.

What is claimed is:

1. A system, comprising:
one or more data processors; and
a non-transitory computer-readable storage medium containing instructions which, when executed on the one or more data processors, cause the one or more data processors to perform operations including:
accessing a latent space mapping usable for encoding data from a plurality of dimensions of an input space into a set of dimensions in a latent space, the latent space mapping being distinct from the latent space, wherein the set of dimensions in the latent space is fewer than the plurality of dimensions of the input space, the latent space mapping being associated with baseline physiological data of one or more subjects in a baseline timeframe, wherein the baseline physiological data in the baseline timeframe is associated with a health condition prior to change, wherein the baseline physiological data includes data across the plurality of dimensions in the input space, and wherein the set of dimensions of the latent space is usable to differentiate one or more features associated with the one or more subjects;

accessing query physiological data of a subject, wherein the query physiological data is associated with a time outside of the baseline timeframe, and wherein the query physiological data includes data across at least some of the plurality of dimensions of the input space;

using the latent space mapping to encode the query physiological data into the latent space, wherein encoding the query physiological data into the latent space results in a representation in the latent space associated with the query physiological data;

using the latent space mapping to decode the representation in the latent space into reconstructed data in the input space;

detecting an anomaly associated with a change in the health condition of the subject using the reconstructed data in the input space; and generating an inference about a parallel variable based on the detected anomaly, wherein the parallel variable is different than the health condition and has an impact on the health condition of the subject.

2. The system of claim 1, wherein detecting the anomaly comprises measuring an amount of error between the query physiological data and the reconstructed data.

3. The system of claim 1, wherein the operations further comprise:
accessing the baseline physiological data;
accessing parallel variable data that is different than the baseline physiological data; and
generating the latent space mapping based on the baseline physiological data and the parallel variable data.

4. The system of claim 3, wherein generating the latent space mapping comprises applying a variational autoencoder or a general adversarial network using the baseline physiological data.

5. The system of claim 3, wherein the baseline timeframe is determined based on the parallel variable data.

6. The system of claim 1, wherein the operations further comprise:
determining a change in the parallel variable independently of the change in the health condition; and
generating the inference based on the change in the parallel variable.

7. The system of claim 1, wherein the operations further comprise:
based on detecting the anomaly, determining whether the subject has experienced a change in the health condition;
in response to determining that the subject has not experienced a change in the health condition, updating the baseline physiological data to include the query physiological data; and generating an updated latent space mapping based on the updated baseline physiological data.

8. The system of claim 1, wherein the operations further comprise:
determining a number of anomalies that were detected with respect to the subject within a preset period of time;
determining that the number of anomalies meets or exceeds a predefined threshold; and
based on the number of anomalies meeting or exceeding the predefined threshold, updating the latent space mapping.

9. The system of claim 1, wherein the operations further comprise:
collecting parallel variable data separately from the baseline physiological data;
determining a number of anomalies that were detected coincident with a same value of the parallel variable; and
inferring that the detected anomaly is caused by the same value of the parallel variable.

10. the system of claim 1, wherein the operations further comprise:
collecting parallel variable data separately from the baseline physiological data; and
in response to detecting a change in the parallel variable data, using the latent space mapping to detect the anomaly.

11. A computer-program product tangibly embodied in a non-transitory machine-readable storage medium, including instructions configured to cause a data processing apparatus to perform operations including:
accessing a latent space mapping usable for encoding data from a plurality of dimensions of an input space into a set of dimensions in a latent space, the latent space mapping being distinct from the latent space, wherein the set of dimensions in the latent space is fewer than the plurality of dimensions of the input space, the latent space mapping being associated with baseline physiological data of a one or more subjects in a baseline timeframe, wherein the baseline physiological data in the baseline timeframe is associated with a health condition prior to change, wherein the baseline physiological data includes data across the plurality of dimensions in the input space, and wherein the set of dimensions of the latent space is usable to differentiate one or more features associated with the one or more subjects;

generate a point cloud in the latent space by encoding the baseline physiological data into the latent space;

accessing query physiological data of a subject, wherein the query physiological data is associated with a time outside of the baseline timeframe, and wherein the query physiological data includes data across at least some of the plurality of dimensions of the input space;

using the latent space mapping to encode the query physiological data into the latent space, wherein encoding the query physiological data into the latent space results in a representation in the latent space associated with the query physiological data;

detecting an anomaly associated with a change in the health condition of the subject by comparing the representation of the query physiological data in the latent space to the point cloud in the latent space; and generating an inference about a parallel variable based on the detected anomaly, wherein the parallel variable is different than the health condition and has an impact on the health condition of the subject.

12. A computer-implemented method, comprising:
accessing a latent space mapping usable for encoding data from a plurality of dimensions of an input space into a set of dimensions in a latent space, wherein the set of dimensions in the latent space is fewer than the plurality of dimensions of the input space, the latent space mapping being associated with baseline physiological data of one or more subjects in a baseline timeframe, wherein the baseline physiological data in the baseline timeframe is associated with a health condition prior to change, wherein the baseline physiological data includes data across the plurality of dimensions in the input space, and wherein the set of dimensions of the latent space is usable to differentiate one or more features associated with the one or more subjects;
accessing query physiological data of a subject, wherein the query physiological data is associated with a time outside of the baseline timeframe, and wherein the query physiological data includes data across at least some of the plurality of dimensions of the input space;
using the latent space mapping to encode the query physiological data into the latent space, wherein encoding the query physiological data into the latent space results in a representation in the latent space associated with the query physiological data;
using the latent space mapping to decode the representation in the latent space into reconstructed data in the input space; detecting an anomaly associated with a change in the health condition of the subject using the reconstructed data in the input space; and
generating an inference about a parallel variable based on the detected anomaly, wherein the parallel variable is different than the health condition and has an impact on the health condition of the subject.

13. The method of claim 12, wherein detecting the anomaly comprises measuring an amount of error between the query physiological data and the reconstructed data.

14. The method of claim 12, further comprising:
accessing the baseline physiological data; and
accessing parallel variable data that is different than the baseline physiological data; and
generating the latent space mapping based on the baseline physiological data and the parallel variable data.

15. The method of claim 14, wherein generating the latent space mapping comprises applying a variational autoencoder or a general adversarial network using the baseline physiological data.

16. The method of claim 12, further comprising:
determining a change in the parallel variable independently of the change in the health condition; and
generating the inference based on the change in the parallel variable.

17. The computer-program product of claim 11, wherein all of the data points in the point cloud relate to a same health condition.

18. The computer-program product of claim 11, wherein the operations further comprise generating the latent space mapping by comprises applying a variational autoencoder or a general adversarial network using the baseline physiological data.

19. The computer-program product of claim 11, wherein the operations further comprise:
determining a change in the parallel variable independently of the change in the health condition; and
generating the inference based on the change in the parallel variable.

20. The computer-program product of claim 11, wherein the operations further comprise:
collecting parallel variable data separately from the baseline physiological data; and
in response to detecting a change in the parallel variable data, using the latent space mapping to detect the anomaly.

* * * * *